United States Patent
Koblish et al.

(10) Patent No.: US 6,217,528 B1
(45) Date of Patent: Apr. 17, 2001

(54) LOOP STRUCTURE HAVING IMPROVED TISSUE CONTACT CAPABILITY

(75) Inventors: Josef V. Koblish, Sunnyvale, CA (US); Boaz Avitall, Milwaukee, WI (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/248,677

(22) Filed: Feb. 11, 1999

(51) Int. Cl.$^7$ .............................. A61B 5/00; A61M 25/00
(52) U.S. Cl. ........................................................... 600/585
(58) Field of Search ................................... 600/585, 434, 600/374, 393, 373

(56) References Cited

U.S. PATENT DOCUMENTS

| | | |
|---|---|---|
| 1,207,479 | 12/1916 | Bisgaard . |
| 4,033,331 * | 7/1977 | Guss et al. ............................ 600/434 |
| 4,181,131 | 1/1980 | Ogiu . |
| 4,245,624 | 1/1981 | Komiya . |
| 4,753,223 | 6/1988 | Bremer . |
| 4,826,087 | 5/1989 | Chinery . |
| 5,041,085 | 8/1991 | Osbourne . |
| 5,098,412 | 3/1992 | Shiu . |
| 5,156,151 | 10/1992 | Imran . |
| 5,263,493 | 11/1993 | Avitall . |
| 5,273,535 | 12/1993 | Edwards . |
| 5,306,245 | 4/1994 | Heavan . |
| 5,368,592 | 11/1994 | Stern . |
| 5,370,675 | 12/1994 | Edwards . |
| 5,399,165 | 3/1995 | Paul, Jr. . |
| 5,415,656 | 5/1995 | Tohon et al. . |
| 5,437,665 | 8/1995 | Munro . |
| 5,439,006 | 8/1995 | Brennen . |
| 5,482,037 | 1/1996 | Borghi . |
| 5,487,385 | 1/1996 | Avitall . |
| 5,487,757 | 1/1996 | Truckai . |
| 5,500,012 | 3/1996 | Brucker . |
| 5,549,661 | 8/1996 | Kordis . |
| 5,637,090 | 6/1997 | McGee . |
| 5,672,174 | 9/1997 | Gough . |
| 5,702,438 | 12/1997 | Avitall . |
| 5,709,224 | 1/1998 | Behl . |
| 5,730,127 | 3/1998 | Avitall . |
| 5,738,683 | 4/1998 | Osypka . |
| 5,782,899 | 7/1998 | Imran . |
| 5,800,482 | 9/1998 | Pomeranz . |
| 5,800,484 | 9/1998 | Gough . |
| 5,820,591 | 10/1998 | Thompson et al. . |
| 5,836,947 | 11/1998 | Fleischman . |
| 5,863,291 | 1/1999 | Schaer . |
| 5,865,800 | 2/1999 | Mirarchi . |
| 5,879,295 | 3/1999 | Li . |

(List continued on next page.)

FOREIGN PATENT DOCUMENTS

| | | |
|---|---|---|
| 3920707A1 | 1/1991 | (DE) . |
| 0238106A1 | 9/1987 | (EP) . |
| 0737487A2 | 10/1996 | (EP) . |
| 0868922 A2 | 10/1998 | (EP) . |
| 0916360A2 | 5/1999 | (EP) . |
| WO97/37607 | 10/1997 | (WO) . |
| WO97/42966 | 11/1997 | (WO) . |
| WO98/26724 | 6/1998 | (WO) . |

OTHER PUBLICATIONS

Jun. 20, 2000 Search Report—PCT appl. Serial No. PCT/US00/03306.

Primary Examiner—Cary O'Connor
Assistant Examiner—Brian Szmal
(74) Attorney, Agent, or Firm—Henricks, Slavin & Holmes LLP

(57) ABSTRACT

A loop structure for supporting operative elements in contact with bodily tissue including an elongate body. The elongate body may include an area with a preset curvature and/or a hinge area.

29 Claims, 6 Drawing Sheets

U.S. PATENT DOCUMENTS

| | | |
|---|---|---|
| 5,910,129 | 6/1999 | Koblish . |
| 5,931,811 | 8/1999 | Haissaguerre . |
| 6,013,052 | 1/2000 | Durman . |
| 6,016,811 | 1/2000 | Knopp . |
| 6,027,473 | 2/2000 | Ponzi . |
| 6,048,329 | 4/2000 | Thompson et al. . |
| 6,071,271 | 6/2000 | Burnside . |
| 6,071,274 | 6/2000 | Thompson . |
| 6,071,279 | 6/2000 | Whayne . |

\* cited by examiner

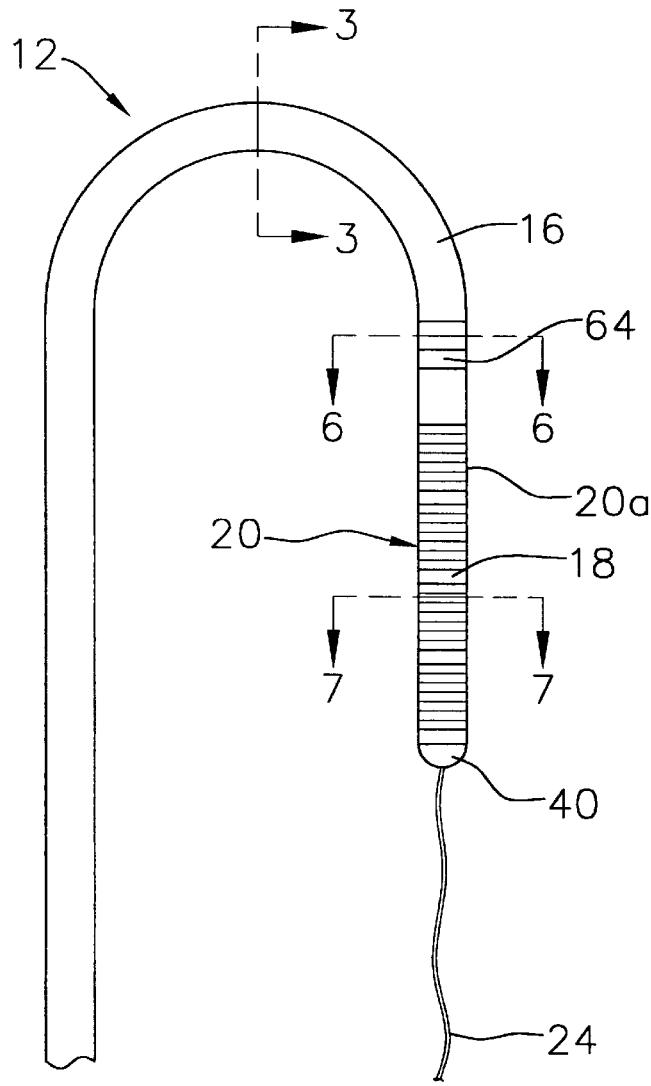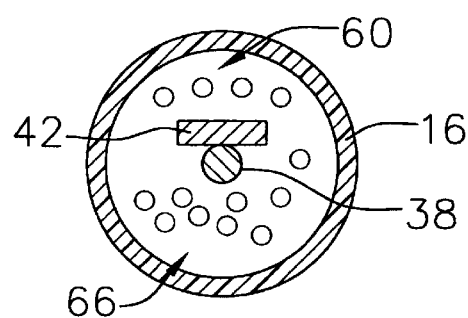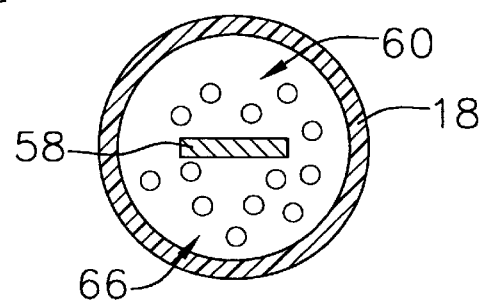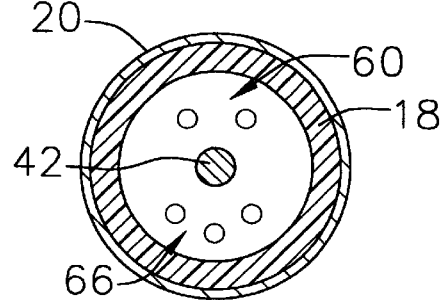

LOOP STRUCTURE HAVING IMPROVED TISSUE CONTACT CAPABILITY

BACKGROUND OF THE INVENTION

1. Field of Inventions

The present invention relates generally to medical devices that support one or more diagnostic or therapeutic elements in contact with body tissue.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the ablation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into loop that extends outwardly from the sheath. This may be accomplished by pivotably securing the distal end of the catheter to the distal end of the sheath, as is illustrated in co-pending U.S. application Ser. No. 08/769,856, filed Dec. 19, 1996, and entitled "Loop Structures for Supporting Multiple Electrode Elements." The loop is formed as the catheter is pushed is the distal direction. The loop may also be formed by securing a pull wire to the distal end of the catheter that extends back through the sheath, as is illustrated in co-pending U.S. application Ser. No. 08/960,902, filed Oct. 30, 1997, and entitled, "Catheter Distal Assembly With Pull Wires," which is incorporated herein by reference. Loop catheters are advantageous in that they tend to conform to different tissue contours and geometries and provide intimate contact between the spaced tissue coagulation electrodes (or other diagnostic or therapeutic elements) and the tissue.

One type of lesion that has proven to be difficult to form with conventional loop catheters is the so-called "flutter lesion" that is used to cure atrial flutter and also forms part of the curative lesion pattern in some instances of atrial fibrillation. The flutter lesion, which blocks a re-entrant pathway that encircles the tricuspid annulus, extends from the inferior vena cava to the tricuspid annulus along the isthmus region of the heart. This area includes a mass of tissue known as the Eustachian ridge. The irregular geometry of the tissue in this area often prevents conventional loop catheters from achieving the level of tissue contact necessary to form a curative lesion. Thus, the flutter lesion must be formed by dragging the tip electrode of a steerable catheter over the target region while the steering mechanism deflects the tip electrode into contact with the tissue. This process must be repeated many times to form a complete lesion with bi-directional block. As a result, and despite the fact that the flutter lesion is relatively short (at 1–2 cm, it is the shortest lesion in the set that cures atrial fibrillation), its formation takes a relatively long time. The flutter lesion typically takes 30 to 60 minutes to complete. To put that in perspective, the lesion that isolates the pulmonary vein, which is about 15 cm in length, also takes about the 30 to 60 minutes to complete.

Accordingly, the inventors herein have determined that a need exists for loop structures that can be used to create lesions within bodily regions, such as the isthmus region of the heart, which have an irregular geometry. In particular, the inventors herein have determined that a need exists for loop structures that can exert enough force on the tissue to form a curative lesion in tissue that has an irregular geometry, such as tissue within the isthmus region of the heart.

SUMMARY OF THE INVENTION

Accordingly, the general object of the present inventions is to provide a device that avoids, for practical purposes, the aforementioned problems. In particular, one object of the present inventions is to provide a device that can be used to create lesions within bodily regions, such as the isthmus region of the heart, which have an irregular geometry. Another object of the present inventions is to provide a device that can be used to quickly create lesions within bodily regions which have an irregular geometry.

In order to accomplish some of these and other objectives, a probe assembly in accordance with one embodiment of a present invention includes an elongate body defining distal region including an operative element and defining at least a first stiffness over a portion thereof and a second stiffness less than the first stiffness over a portion thereof proximal to the operative element, and a control element associated with the distal end of the elongate body and extending along the exterior of the elongate body.

In order to accomplish some of these and other objectives, a probe assembly in accordance with one embodiment of a present invention includes an outer member and an elongate body carried within the outer member, the distal region of the elongate body being configured such that, when deployed from the outer member, it will assume a loop configuration having a curved portion and a substantially linear portion.

In order to accomplish some of these and other objectives, a probe assembly in accordance with one embodiment of a present invention includes an elongate body defining a distal region including an operative element and a portion with a preset curvature proximal to the operative element, and a control element associated with to the distal end of the elongate body and extending along the exterior of the elongate body. The elongate body may, for example, be a one-piece apparatus such as a catheter body. The elongate body may, for example, also be in the form of a two-piece apparatus including a tubular member having the portion with a preset curvature and a catheter body that carries the operative element and is located within the tubular member.

The present probe embodiments provide a number of advantages over conventional apparatus. For example, the present probes may be used to create therapeutic lesions over tissue areas that have irregular surfaces and areas that are located in areas that make the application of desirable levels of force difficult.

One implementation of a probe in accordance with the inventions herein is a loop catheter used in the formation of flutter lesions on the isthmus region of the heart between the inferior vena cava and the tricuspid annulus. When the distal portion of the elongate body is deployed within the atrium, the portion having a preset curvature will rest against the roof of the atrium while straddling the isthmus region, thereby providing a fixed leverage point in an optimal location. In addition, a hinged area will be formed proximal to the proximal-most operative element, such as an electrode, and the operative element carrying portion of the elongate body, which is distal to the hinged area, will remain substantially linear. In this orientation, the portion of the elongate body carrying the operative elements will be positioned over the isthmus region. Next, when tension force is applied to the control element by the physician, the portion of the elongate body carrying the operative elements will press against the tissue in the isthmus region. Additional tension force may be applied through the elongate body. Ultimately, the portion of the elongate body carrying the operative elements will compress the tissue and flatten the irregularly shaped Eustachian ridge to some extent as it bends and conforms to the contour of the compressed tissue.

As a result, a loop catheter in accordance with the inventions herein provides excellent tissue/electrode contact. Additionally, a larger percentage of the total surface area of the electrodes will be in contact with the tissue than has been achieved with conventional loop catheters. This results in deeper lesions with less convective cooling than conventional loop catheters. The inventions herein also provide a significant mechanical advantage over steerable catheters, which rely on their internal steering mechanisms to generate tissue contact force. The inventions herein also enable the formation lesions with bi-directional block in significantly less time than those which can be produced by dragging the tip electrode of a steerable catheter over tissue.

The above described and many other features and attendant advantages of the present invention will become apparent as the invention becomes better understood by reference to the following detailed description when considered in conjunction with the accompanying drawings.

BRIEF DESCRIPTION OF THE DRAWINGS

Detailed description of preferred embodiments of the invention will be made with reference to the accompanying drawings.

FIG. 2 is a side view of a portion of the probe illustrated in FIG. 1 in an unstressed state.

FIG. 3 is a section view taken along line 3—3 in FIG. 2.

FIG. 6 is a section view taken along line 6—6 in FIG. 2.

FIG. 7 is a section view taken along line 7—7 in FIG. 2.

DETAILED DESCRIPTION OF THE PREFERRED EMBODIMENTS

Figure 1:
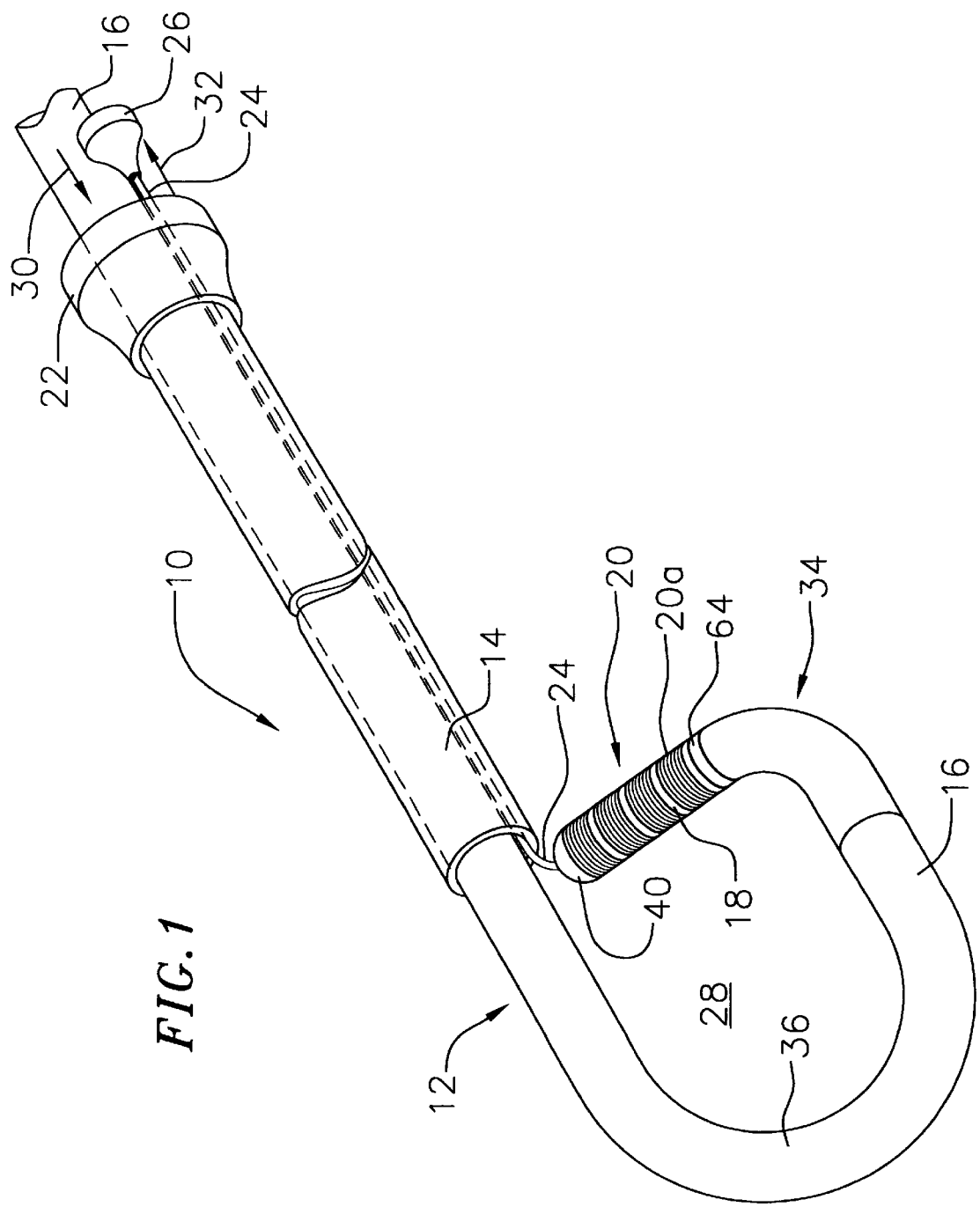
FIG. 1 is perspective view of a probe in accordance with a preferred embodiment of the present invention.
Figure 4:
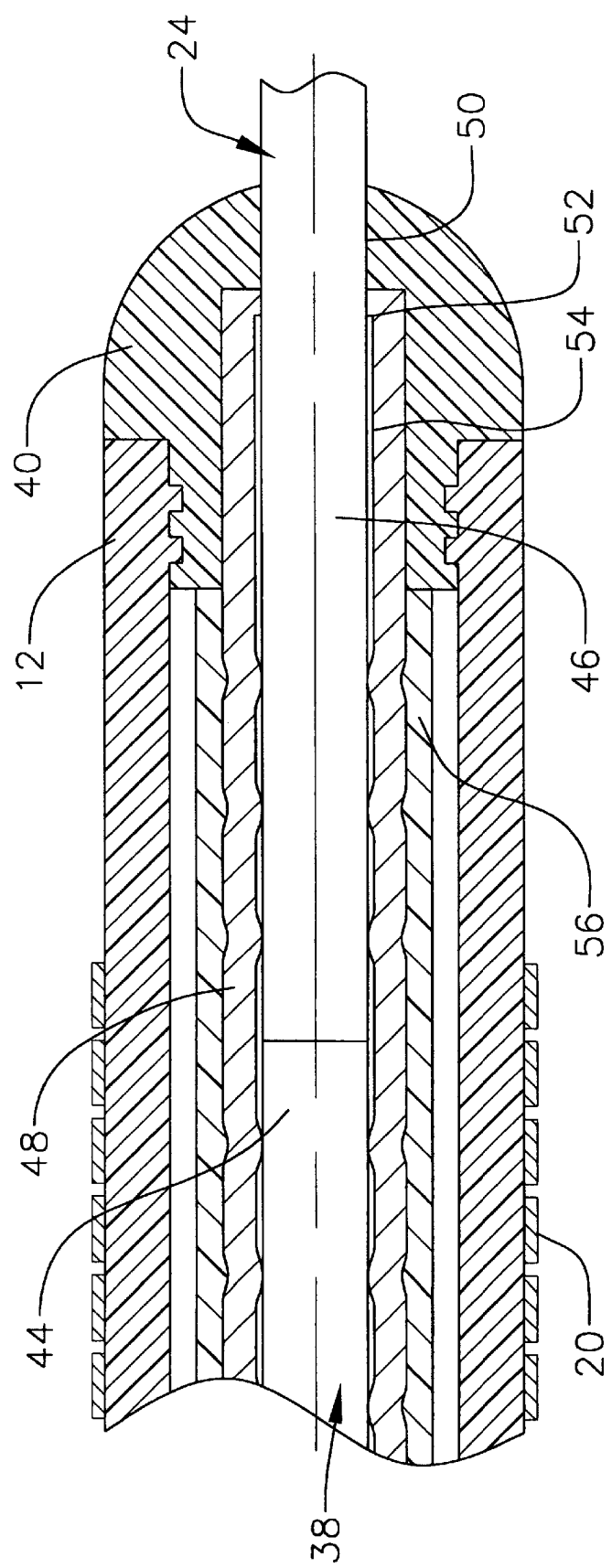
FIG. 4 is a side, partial section view of a portion of the probe illustrated in FIG. 1.

The following is a detailed description of the best presently known mode of carrying out the invention. This description is not to be taken in a limiting sense, but is made merely for the purpose of illustrating the general principles of the invention.

The detailed description of the preferred embodiments is organized as follows:

I. Introduction

II. Probe Structures

III. Electrodes, Temperature Sensing and Power Control

The section titles and overall organization of the present detailed description are for the purpose of convenience only and are not intended to limit the present invention.

I. Introduction

The present inventions may be used within body lumens, chambers or cavities for diagnostic or therapeutic purposes in those instance where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body.

With regard to the treatment of conditions within the heart, the present inventions are designed to produce intimate tissue contact with target substrates associated with various arrhythmias, namely atrial fibrillation, atrial flutter, and ventricular tachycardia. For example, the distal portion of a catheter in accordance with a present invention, which may include diagnostic and/or soft tissue coagulation electrodes, will conform to non-uniform anatomic regions such as the Eustachian ridge between the inferior vena cava and the tricuspid annulus.

The structures are also adaptable for use with systems that are not necessarily catheter-based. For example, the structures disclosed herein may be used in conjunction with hand held surgical devices (or "surgical probes"). The distal end of a surgical probe may be placed directly in contact with the targeted tissue area by a physician during a surgical procedure, such as open heart surgery for mitral valve replacement. Here, access may be obtained by way of a thoracotomy, median sternotomy, or thoracostomy. Exemplary surgical probes are disclosed in co-pending U.S. application Ser. No. 09/072,872, filed May 5, 1998, and entitled "Surgical Methods and Apparatus for Positioning a Diagnostic or Therapeutic Element Within the Body."

Surgical probe devices in accordance with the present invention preferably include a handle, a relatively short shaft, and one of the distal assemblies described hereafter in the catheter context. Preferably, the length of the shaft is about 4 inches to about 18 inches. This is relatively short in comparison to the portion of a catheter body that is inserted into the patient (typically from 23 to 55 inches in length) and the additional body portion that remains outside the patient. The shaft is also relatively stiff. In other words, the shaft is either rigid, malleable, or somewhat flexible. A rigid shaft cannot be bent. A malleable shaft is a shaft that can be readily bent by the physician to a desired shape, without springing back when released, so that it will remain in that shape during the surgical procedure. Thus, the stiffness of a malleable shaft must be low enough to allow the shaft to be bent, but high enough to resist bending when the forces associated with a surgical procedure are applied to the shaft. A somewhat flexible shaft will bend and spring back when released. However, the force required to bend the shaft must be substantial.

II. Probe Structures

As illustrated for example in FIG. 1, a probe 10 in accordance with a preferred embodiment of the present invention includes a hollow, flexible catheter body 12 that passes through the lumen of a sheath 14 (or other outer tubular member). The catheter body 12 is preferably formed from two tubular parts, or members. The proximal member 16 is relatively long and is attached to a handle (not shown), while the distal member 18, which is relatively short, carries a plurality of spaced electrodes 20 or other operative elements. The proximal member 16 is typically formed from a biocompatible thermoplastic material, such as a Pebax® material (polyether block emide) and stainless steel braid composite, which has good torque transmission properties. In some implementations, an elongate guide coil (not shown) may also be provided within the proximal member 16. The distal member 18 is typically formed from a softer, more flexible biocompatible thermoplastic material such as unbraided Pebax® material, polyethylene, or polyurethane. The proximal and distal members are preferably either bonded together with an overlapping thermal bond or adhesive bonded together end to end over a sleeve in what is referred to as a "butt bond."

The exemplary sheath 14, which has a handle 22 at the proximal end thereof, preferably includes a number of preset curves that allow it to be guided to a predetermined anatomical location. Of course, other types of sheaths, such as those which are carried by a steerable catheter to the targeted region and those which include there own steering mechanisms, may also be used. The sheath 14 should have a greater inherent stiffness than the distal region of the catheter body 12, which includes the distal member 18, the electrodes 20 and a spline 38 that is discussed below with reference to FIGS. 3–7. The sheath 14 should also be lubricious to reduce friction during movement of the catheter body 12. With respect to materials, the sheath 14 is preferably a Pebax® and stainless steel braid composite. Other materials, such as polytetrafluoroethylene (PTFE), can also be used. The wall thickness of the sheath 14 is preferably about 0.013 inch, which will not add significantly to the overall thickness of the probe 10.

In the exemplary embodiment illustrated in FIG. 1, the distal end of the sheath 14 is perpendicular to the longitudinal axis of the sheath. However, the distal end of the sheath 14 may also be cut at an angle and tapered in a transverse direction relative to the longitudinal axis of the sheath.

A pull wire 24 extends from the distal end of the catheter body 12 through the sheath 14 in the exemplary embodiment illustrated in FIG. 1. The proximal end of the pull wire 24 includes a stop/handle 26. The pull wire 24 is preferably a flexible, inert cable constructed from strands of metal wire material, such as Nickel Titanium (commercially available under the trade name Nitinol®) or 17-7 stainless steel, that is about 0.012 to 0.018 inch in diameter. Alternatively, the pull wire 24 may be formed from a flexible, inert stranded or molded plastic material. The pull wire 24 is also preferably round in cross-section, although other cross-sectional configurations can be used.

Holding the handle 26 stationary, the physician deploys a loop structure 28 by advancing the catheter body 12 through the sheath 14 (arrow 30). Once the loop structure 28 has been formed, the physician can pull on the wire 24 (arrow 32) to decrease the exposed length of the pull wire beyond the distal end of the sheath 14. Further adjustments to the loop may be made by advancing or retracting the catheter body 12 within the sheath 14 or by putting tension on the pull wire 24. For example, retracting the catheter body 12 to the position illustrated in FIG. 1 and pulling the pull wire to its retracted position will cause the distal member 18 to deflect at a hinge area (or "area of reduced stiffness") 34. This aspect of the invention is discussed in greater detail below with reference to FIGS. 1, 2 and 5. In addition, the loop structure 28 can be rotated by rotating the catheter body 12 with its handle (not shown) or by rotating the sheath 14 with the its handle 22.

In accordance with an invention herein, the catheter body proximal member 16 includes include a region 36 with a preset curve. In other words, once the region 36 is advanced beyond the sheath 14, it will bend into a preset curved configuration. As illustrated for example in FIGS. 1 and 2, the curved region 36 is preferably substantially semicircular (or u-shaped). Although the present semicircular curvature is especially well suited for the atrium and lesion formation along the Eustachian ridge between the inferior vena cava and the tricuspid annulus, the curvature may be varied to suit particular applications. The radius of the curved region 36 in the exemplary embodiment is approximately 1.5 inches. The preset curvature may be accomplished in a variety of manners. Preferably, the curved region 36 of the catheter body proximal member 16 is preset through use of a thermal forming technique (100° C. for 1 hour).

As illustrated in FIGS. 3–7, the exemplary catheter body 12 also includes a flexible spline (or "core wire") 38. The flexible spline 38 is preferably a wire having a diameter of approximately 0.023 inch that is positioned inside of and passes within the length of the catheter body 12. The flexible spline 38 is fixedly secured to the handle at the proximal end of the catheter body 12 and to a tip member 40, as is described below, which is in turn secured to the distal end of the catheter body with adhesive. In the preferred embodiment, the flexible spline 38 is made from resilient, inert wire, such as Nitinol® material or 17-7 stainless steel. Resilient injection molded plastic can also be used. The exemplary spline 38 is round in cross section, although other cross sectional configurations can be used.

In addition to the presetting of the proximal member 16, or as an alternative, the flexible spline 38 may also have a preset curvature. The spline curvature is thermally preset at 500° C. for 8 minutes. However, the super-elastic properties of the material should be maintained. Where a round cross section spline 38 is employed, a thin, rectilinear strip 42 (FIG. 3) of resilient metal (preferably 17-7 stainless steel) or plastic material that is also preset into the desired curvature may be secured to the flexible spline with, for example, heat shrink tubing (not shown). The rectilinear strip 42 reinforces the curved region 36 and prevents it from being too easily deflected when pressure is applied to the loop structure.

The flexible spline 38 may also be used to anchor the pull wire 24. As illustrated for example in FIG. 4, the distal end 44 of the flexible spline 38 is fixedly engaged in an in-line manner to the distal end 46 of the pull wire 24 with a stainless steel crimp tube 48. The in-line connection of flexible spline 38 and pull wire 24 allows for a reduction in the overall diameter of distal portion of the catheter body 12. This provides a significant clinical advantage over devices having side by side pull wire connections which create a larger diameter device. The pull wire 24 passes through a pull wire bore 50 in the catheter tip member 40 and through a bore 52 in the distal end 54 of the crimp tube 48. The tip 40 member is preferably formed from platinum and is fixedly engaged with, for example, silver solder, adhesive or spot welding, to the distal end 54 of crimp tube 48. The flexible spline 38 is preferably electrically insulated with a thin walled polyester heat shrink tube 56 that extends beyond the proximal end of the crimp tube 48. Other pull wire configurations, other methods of attaching the pull wire to the catheter body, and methods of reducing stress on the pull wire are disclosed in aforementioned U.S. application Ser. No. 08/960,902.

In accordance with another invention herein, the hinge area 34 of the exemplary catheter body 12 may be located proximally of the proximal-most electrode 20a. In the preferred embodiment, and as illustrated for example in FIGS. 5 and 6, a portion of the flexible spline 38 is deformed to form the hinge area 34. More specifically, the flexible spline 38 preferably includes a flattened portion 58 which causes the distal portion of the catheter body 12 to deflect in the manner shown in FIG. 1. The flattened portion is about 0.5 inch in length and has a thickness of less than approximately 0.010 inch, which is a significant reduction as compared to the 0.023 inch diameter of the remainder of the flexible spline 38 and make the flattened portion more flexible in the bending plane. Distal to the flattened portion 58, the flexible spline 38 regains its circular cross section, as is shown in FIG. 7. As a result, the portion of the catheter body 12 distal to the flattened portion 58 will, absent the application of other forces, remain linear when the flattened portion 58 is bent.

The hinge area 34 may be formed in other ways. For example, the hinge area 34 may be formed by simply removing a section of the flexible spline 38 in the hinge area.

The combination of the flattened portion 58 of the flexible spline 38, its location, and the curved region 36 of the catheter body proximal member 16 provides a loop structure that predictability and consistently approximates the interior of the atrium and facilitates the production of therapeutic lesions along the isthmus region between the inferior vena cava and the tricuspid annulus. As illustrated for example in FIG. 8, after the distal end of the sheath 14 reaches the atrium, the distal portion of the catheter body 12 is deployed. A portion of the proximal member curved region 36 will rest against the roof of the atrium while straddling the isthmus region, thereby providing a fixed leverage point in an optimal location, and the distal member 18 will bend at the hinge area 34. The application of tension force to the pull wire 24 will cause the distal portion of the catheter body 12, which is linear distal to the hinge area 34 when unstressed, to press against the tissue in the isthmus region.

Figure 8:
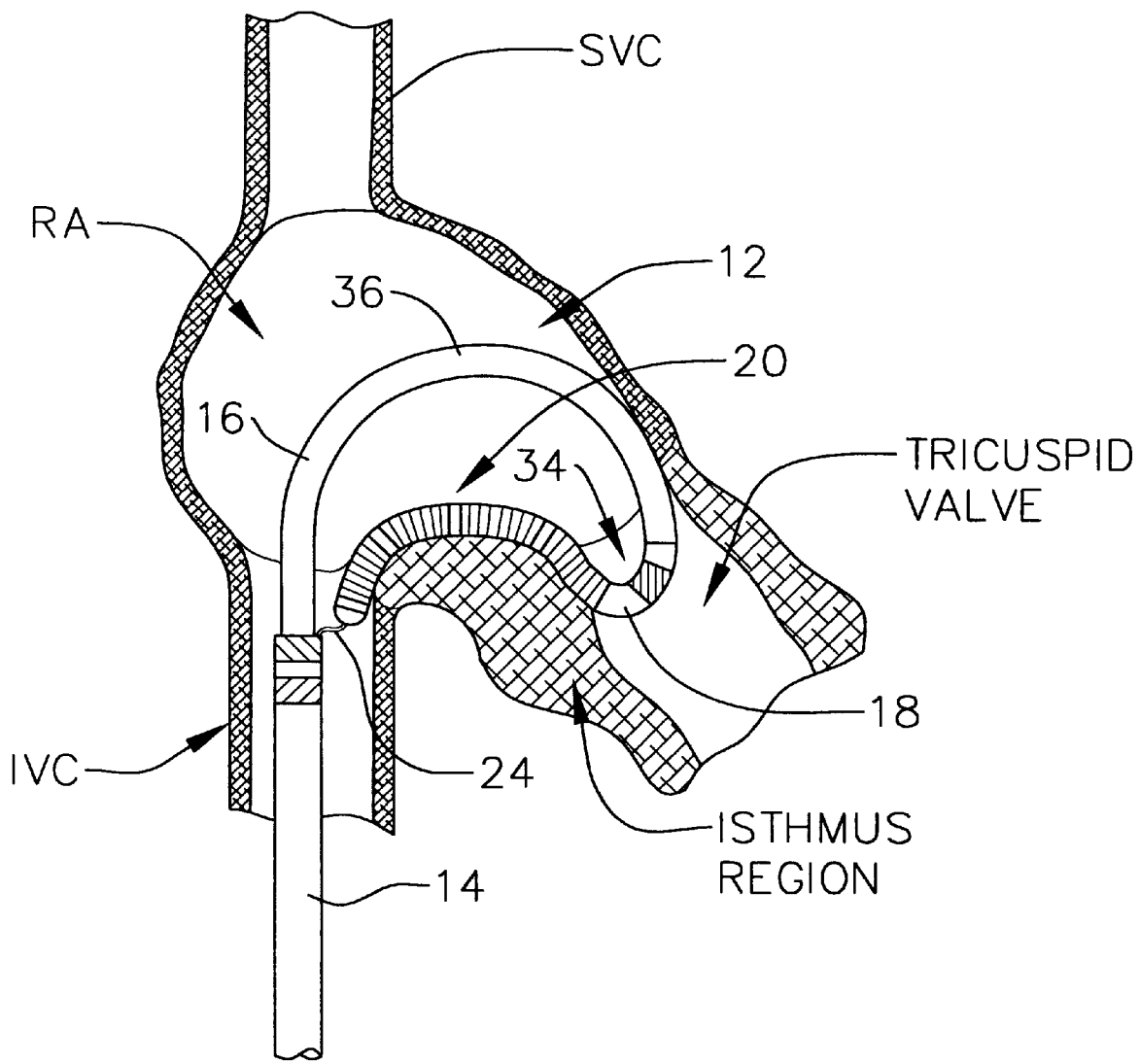
FIG. 8 is a partial section view showing the probe illustrated in FIG. 1 deployed in the right atrium.

When sufficient force is applied, either by way of the application of tension force to the pull wire 24 alone or by way of the application of tension force to both the catheter body 12 and the pull wire, the distal region of the catheter body 12 will compress the tissue (and flatten the irregularly shaped Eustachian ridge) in the manner illustrated in FIG. 8. The distal region will also bend and conform to the contour of the compressed tissue. The result is excellent tissue/ electrode contact and a larger percentage of the total surface area of the electrodes in contact with the tissue than has been achieved with conventional loop catheters. Accordingly, the present invention provides deeper lesions with less convective cooling than conventional loop catheters.

Figure 9:
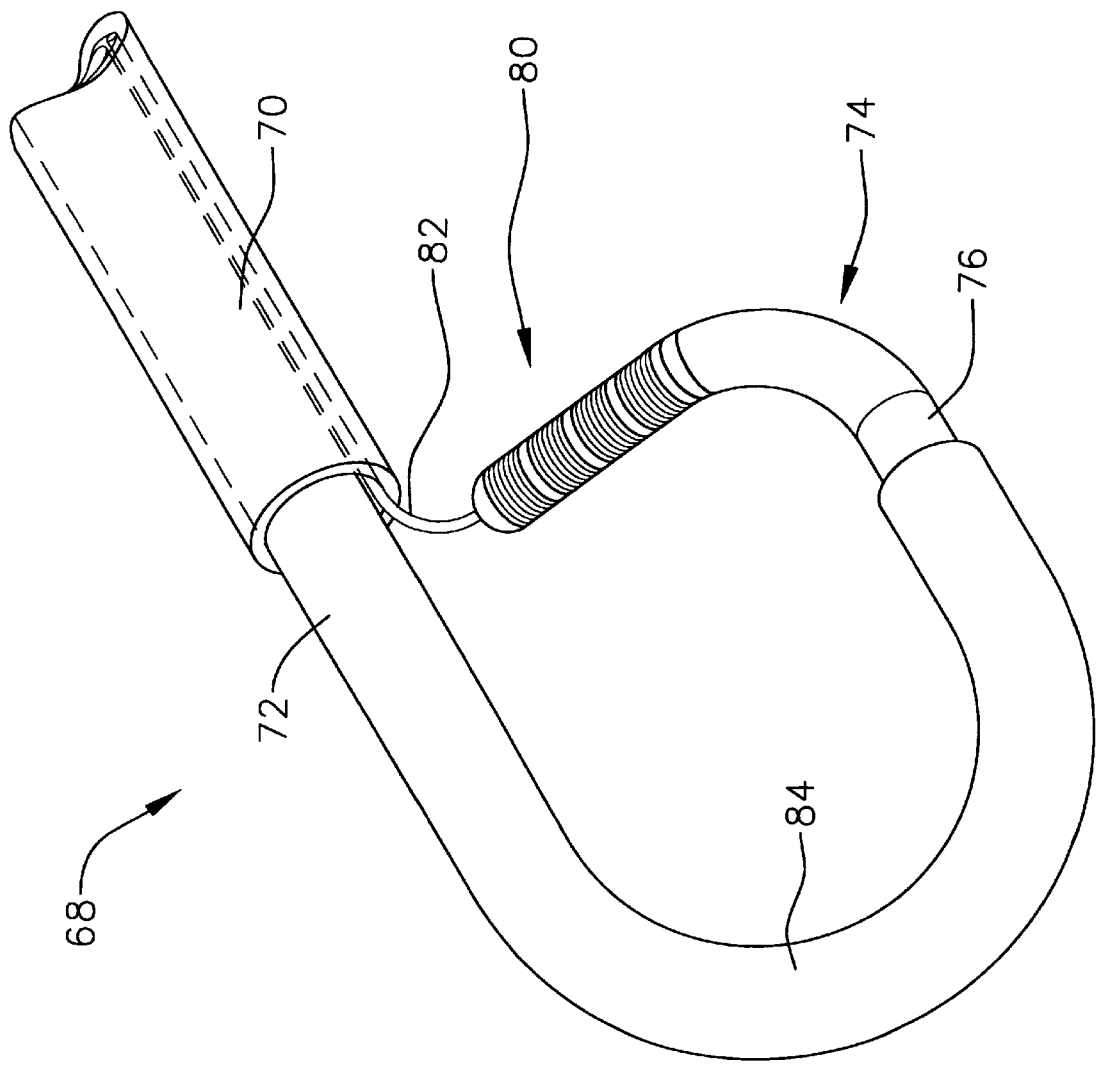
FIG. 9 is partial perspective view of a probe in accordance with another preferred embodiment of the present invention.

Another exemplary probe structure capable of performing in the manner described above is illustrated in FIG. 9. The probe structure, which is generally represented by reference number 68, includes a first sheath 70 (or other tubular member), a second sheath 72 (or other tubular member) that passes through the lumen in the first sheath, and a flexible catheter body 74 that passes through the lumen in the second sheath. The catheter body 74 is substantially similar to the catheter body 12 in that it includes, among other things, a relatively long proximal member 76 with good torque transmission properties, a relatively short, flexible distal member 78 that carries a plurality of spaced electrodes 80 or other operative elements, and a pull wire 82. However, the catheter body 74 does not necessarily include the preformed curved region that can be used, for example, to rest against the roof of the atrium. In the exemplary embodiment illustrated in FIG. 9, the second sheath 72 includes a preformed curved distal region 84 that performs essentially the same function as the preformed curved region 36 of the catheter illustrated in FIGS. 1–8. The curvature of the distal region 84 may be produced through the use of thermal forming techniques.

The first sheath 70 in the exemplary probe structure 68 has a greater inherent stiffness that the second sheath 72 and the second sheath has a greater inherent stiffness than the catheter body distal member 78. The second sheath 72 will assume the shape of the first sheath 70 until the second sheath is advanced beyond the distal opening of the first sheath. At that time, the distal region of the second sheath 72 will assume its preformed curved shape. When the catheter body 74 is deployed and tension is applied to the pull wire 82, the probe structure 68 will assume the configuration illustrated in FIG. 9.

It should also be noted that a hinge structure similar to the hinge 34 described above is not necessary in the probe structure 68. The relative stiffness' of distal region of the second sheath 72 and the catheter body distal member 78 are preferably such that the application of tension to the pull wire 82 will result in the abrupt bend in the catheter body 74 illustrated in FIG. 9.

III. Electrodes, Temperature Sensing and Power Control

In the preferred embodiment, the operative elements are a plurality of spaced electrodes. However, other operative elements, such as lumens for chemical ablation, laser arrays, ultrasonic transducers, microwave electrodes, and D.C. hot wires, and such devices may be substituted for the electrodes.

The spaced electrodes 20 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905. The electrodes 20 are electrically coupled to individual wires 60 (FIGS. 3, 6 and 7) to conduct coagulating energy to them. The wires are passed in conventional fashion through a lumen extending through the catheter body 12 into a PC board in the catheter handle, where they are electrically coupled to a connector that is received in a port on the handle. The connector plugs into a source of RF coagulation energy.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 20 are preferably about 4 mm to about 20 mm in length. In the preferred embodiment, the electrodes are 12.5 mm in length with 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

Figure 5:
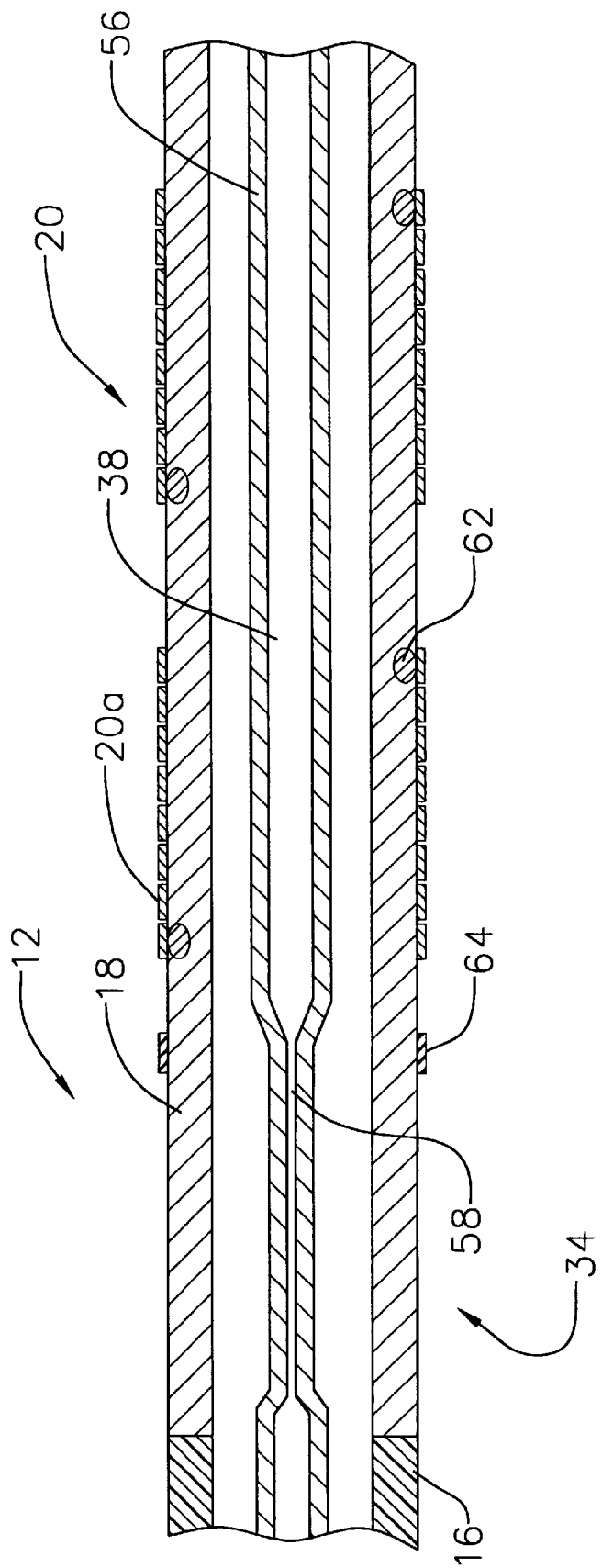
FIG. 5 is a side, partial section view of a portion of the probe illustrated in FIG. 1.

As illustrated for example in FIG. 5, a plurality of temperature sensors 62, such as thermocouples or thermistors, may be located on, under, abutting the longitudinal end edges of, or in between, the electrodes 20. In some embodiments, a reference thermocouple 64 may also be provided. For temperature control purposes, signals from the temperature sensors are transmitted to the source of coagulation energy by way of wires 66 that are also connected to the aforementioned PC board in the catheter handle. Suitable temperature sensors and controllers which control power to electrodes based on a sensed temperature are disclosed in U.S. Pat. Nos. 5,456,682, 5,582,609 and 5,755,715.

Finally, the electrodes 20 and temperature sensors 62 can include a porous material coating, which transmits coagulation energy through an electrified ionic medium. For example, as disclosed in U.S. application Ser. No. 08/879, 343, filed Jun. 20, 1997, entitled "Surface Coatings For Catheters, Direct Contacting Diagnostic and Therapeutic Devices," electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

Although the present invention has been described in terms of the preferred embodiments above, numerous modifications and/or additions to the above-described preferred embodiments would be readily apparent to one skilled in the art. It is intended that the scope of the present invention extends to all such modifications and/or additions and that the scope of the present invention is limited solely by the claims set forth below.

We claim:

1. A probe assembly, comprising:
   an outer member including a wall defining an interior bore having a distal end and a proximal end;
   an elongate body, defining a distal region, a distal end, a proximal end and an exterior, carried within the outer member, the distal region of the elongate body including a plurality of operative elements, one of the operative elements defining a proximal-most operative element, and the distal region defining at least a first stiffness over a substantial portion thereof and a second stiffness, less than the first stiffness, over a portion thereof that is proximal to the proximal-most operative element; and
   a control element defining a distal portion associated with the distal end of the elongate body and a proximal portion extending along the exterior of the elongate body within the outer member toward the proximal end of the outer member.

2. A probe assembly as claimed in claim 1, wherein the outer member comprises a tubular sheath.

3. A probe assembly as claimed in claim 1, wherein the control element comprises a pull wire.

4. A probe assembly as claimed in claim 1, wherein the elongate body comprises a catheter body.

5. A probe assembly as claimed in claim 1, wherein the elongate body includes a flexible spline extending from adjacent the distal end toward the proximal end.

6. A probe assembly as claimed in claim 5, wherein the flexible spline comprises a solid core wire.

7. A probe assembly as claimed in claim 6, wherein the flexible spline defines a first cross sectional shape over a substantial portion thereof and a second cross sectional shape over a relatively small portion thereof.

8. A probe assembly as claimed in claim 7, wherein the first cross-sectional shape is substantially circular and the second cross sectional shape is substantially flat.

9. A probe assembly as claimed in claim 1, wherein the plurality of operative elements comprises a plurality of electrodes.

10. A probe assembly as claimed in claim 1, wherein the elongate body defines at least the first stiffness from the distal end to the portion defining the second stiffness.

11. A probe assembly as claimed in claim 1, wherein the electrodes are coextensive with the substantial portion of the distal region.

12. A probe assembly as claimed in claim 1, wherein the distal region defines a bending plane and the first and second stiffness are measured in the bending plane.

13. A probe assembly, comprising:
an outer member including a wall defining an interior bore having a distal end and a proximal end;
an elongate body, defining a distal region, a distal end, a proximal end and an exterior, carried within the outer member, the distal region of the elongate body including an operative element and a hinge and being configured such that, when deployed from the distal end of the outer member with the distal end of the elongate body closely adjacent the distal end of the outer member, it will assume a loop configuration having a curved portion proximal of the hinge and a substantially linear portion distal of the curved portion and the hinge; and
a control element defining a distal portion associated with to the distal end of the elongate body and a proximal portion extending along the exterior of the elongate body within the outer member toward the proximal end of the outer member.

14. A probe assembly as claimed in claim 1, wherein the outer member comprises a tubular sheath.

15. A probe assembly as claimed in claim 1, wherein the control element comprises a pull wire.

16. A probe assembly as claimed in claim 1, wherein the elongate body comprises a catheter body.

17. A probe assembly as claimed in claim 1, wherein the operative element comprises an electrode.

18. A probe assembly as claimed in claim 1, wherein the operative element is located along the substantially linear portion of the loop.

19. A probe assembly as claimed in claim 1, wherein the operative element comprises a plurality of operative elements located along the substantially linear portion of the loop.

20. A probe assembly as claimed in claim 1, wherein the distal region is configured such that it will be substantially D-shaped when the distal end of the elongate body is closely adjacent the distal end of the outer member and the substantially linear portion is substantially perpendicular to the longitudinal axis of the interior bore.

21. A probe assembly as claimed in claim 20, wherein the operative element comprises a plurality of electrodes on the substantially linear portion.

22. A probe assembly as claimed in claim 13, wherein the curved portion has a preset curvature.

23. A probe assembly, comprising:
an outer member including a wall defining an interior bore having a distal end and a proximal end;
an elongate body, defining a distal region, a distal end, a proximal end and an exterior, carried within the outer member, the distal region of the elongate body including a portion with a present curvature and a portion supporting a plurality of operative elements, one of the operative elements defining a proximal-most operative element, the elongate body further including a flexible spline located therein and extending from adjacent the distal end toward the proximal end, the flexible spline defining a first stiffness over a first spline portion coextensive with the plurality of operative elements and a second stiffness over a spline second portion located proximal to the proximal-most operative element, the second stiffness being less than the first stiffness; and
a control element defining a distal portion associated with the distal end of the elongate body and a proximal portion extending along the exterior of the elongate body within the outer member toward the proximal end of the outer member.

24. A probe assembly as claimed in claim 23, wherein the outer member comprises a tubular sheath.

25. A probe assembly as claimed in claim 23, wherein the control element comprises a pull wire.

26. A probe assembly as claimed in claim 23, wherein the elongate body comprises a catheter body.

27. A probe assembly as claimed in claim 23, wherein the operative elements comprise electrodes.

28. A method of positioning a operative element adjacent tissue between the inferior vena cava and the tricuspid annulus, comprising the steps of:
providing an outer member including a wall defining an interior bore and having a distal end and a proximal end;
providing an elongate apparatus defining a distal end and a distal region that supports the operative element spaced from the elongate body distal end and a region with a preset curvature having a distal end proximal to the operative element;
providing a control element associated with the distal region of the elongate apparatus;
advancing the outer member into the heart;
advancing the elongate apparatus through the interior bore of the outer member and into the heart such that the distal region of the elongate apparatus extends beyond the distal end of the outer member and assumes the preset curvature with the distal end of the region with a preset curvature adjacent the tricuspid annulus;
applying tension to the control element to pull the distal end of the elongate apparatus closely adjacent to the distal end of the outer member; and
applying tension to at least one of the control element and the elongate apparatus when the distal end of the elongate apparatus is closely adjacent to the distal end of the outer member to pull the operative element into contact with the tissue between the inferior vena cava and tricuspid annulus.

29. A probe assembly as claimed in claim 23, wherein the distal region defines a bending plane and the first and second stiffness are measured in the bending plane.

* * * * *